United States Patent [19]

Wimmer

[11] Patent Number: 4,799,886
[45] Date of Patent: Jan. 24, 1989

[54] DENTAL SUBMERGED ENDOSSEOUS IMPLANT

[75] Inventor: Joachim Wimmer, Fort Lee, N.J.

[73] Assignee: Park Dental Research Corp., New York, N.Y.

[21] Appl. No.: 39,537

[22] Filed: Apr. 16, 1987

[51] Int. Cl.⁴ .............................................. A61C 8/00
[52] U.S. Cl. .................................................... 433/176
[58] Field of Search ................ 433/173, 174, 175, 176

[56] References Cited

U.S. PATENT DOCUMENTS

| | | | |
|---|---|---|---|
| 4,109,383 | 8/1978 | Reed | 433/176 |
| 4,187,609 | 2/1980 | Edelman | 433/176 |
| 4,217,100 | 8/1980 | Edelman | 433/176 |
| 4,661,066 | 9/1987 | Linkow et al. | 433/176 |

OTHER PUBLICATIONS

Core Vent Corp., pp. 57 and 58, 16030 Venting Blvd, Encino, Calif., 91436.

Primary Examiner—Robert Peshock
Attorney, Agent, or Firm—Eliot S. Gerber

[57] ABSTRACT

A dental implant is a submerged endosseous implant system and a blade implant is an integral one-piece body member having a blade-like portion, a collar support portion, and one or more cylindrical tubular collars, with each cylindrical collar having an internal screw-threaded bore. After the blade body member is positioned in the groove in the patient's jaw a short flat healing plug is screwed into the collar bore and the gum sutured and allowed to heal. After healing, the flat-headed plug is removed and an abutment head is screwed into the collar bore, the head including an externally threaded shaft portion and a head portion having a groove. The top head portion may be bent at the groove to obtain the desired head angle. The same type of abutment head is used with a submerged screw implant.

4 Claims, 4 Drawing Sheets

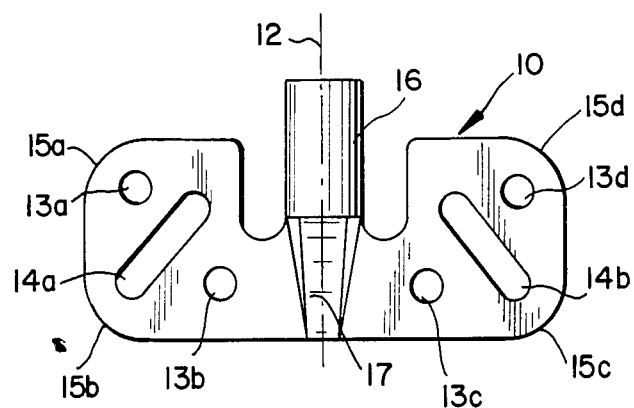
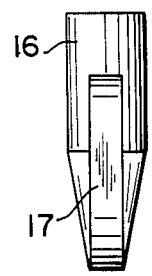
FIG. 1
FIG. 2
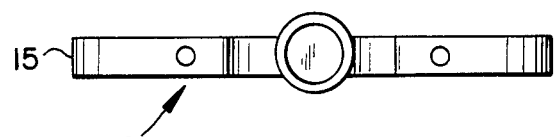
FIG. 3
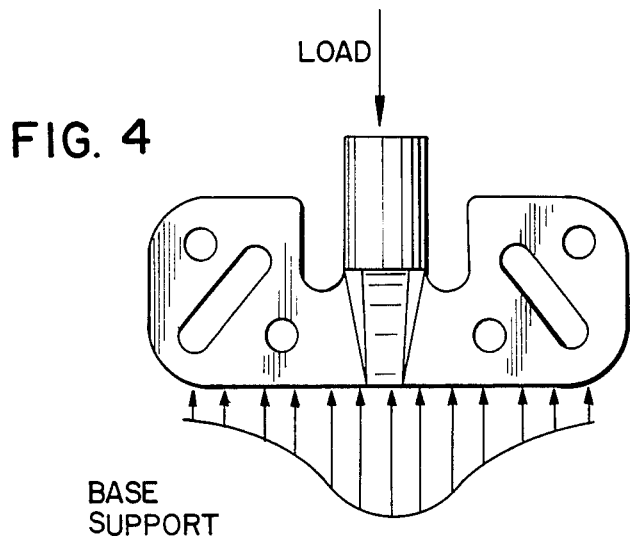
FIG. 4

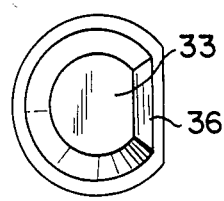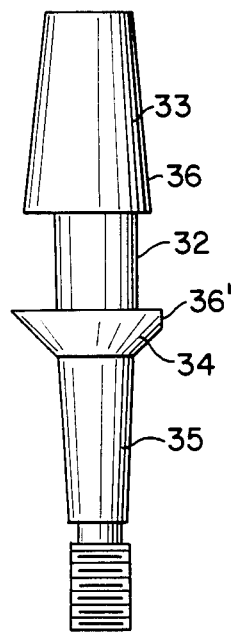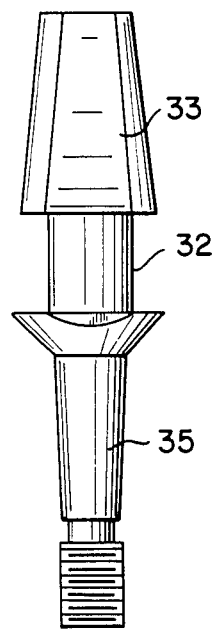
FIG. 7B   FIG. 7   FIG. 7A
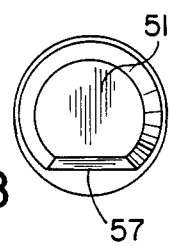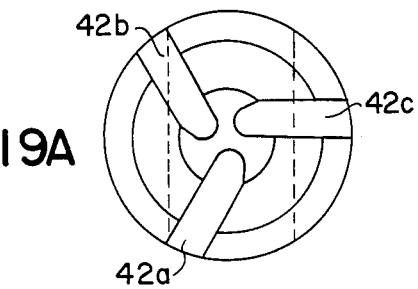
FIG. 20B   FIG. 19A
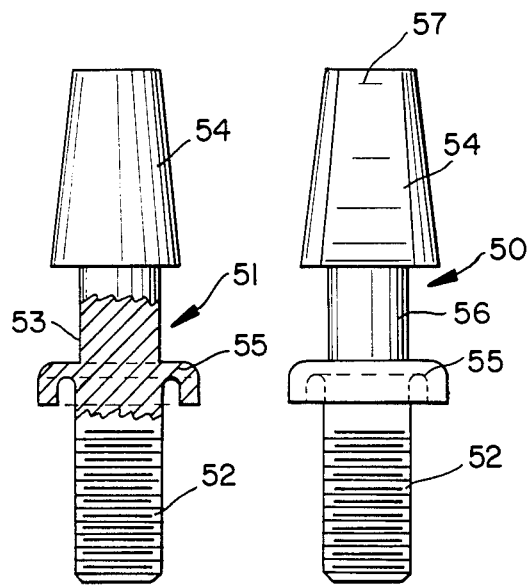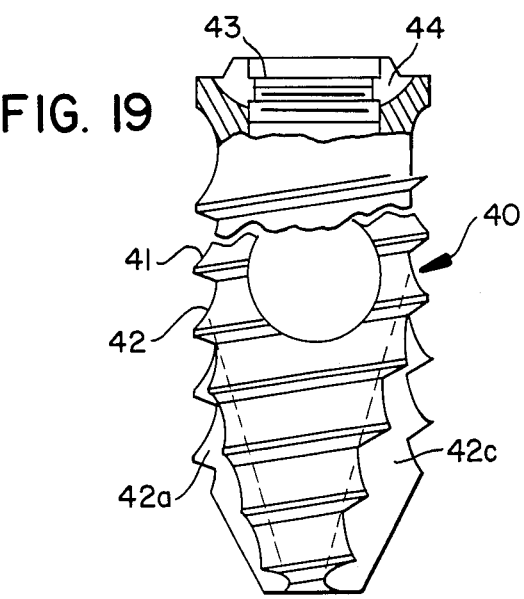
FIG. 20   FIG. 20A   FIG. 19

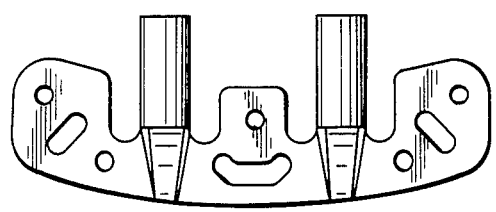
FIG. 12
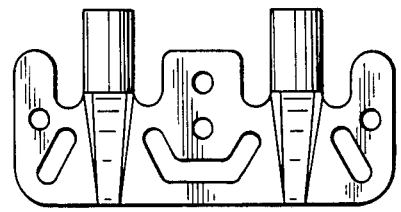
FIG. 16
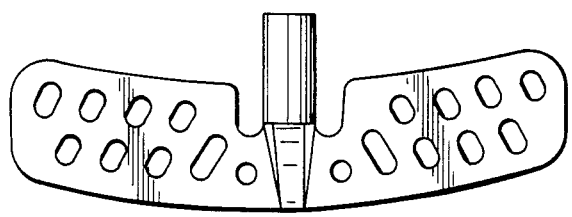
FIG. 13
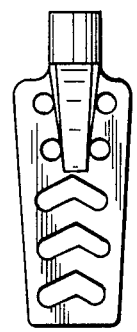
FIG. 17
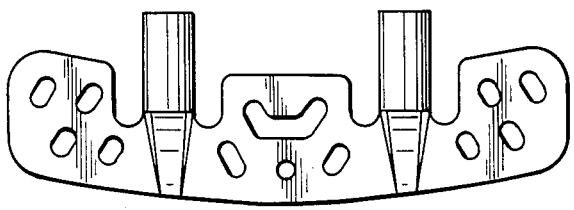
FIG. 14
FIG. 15
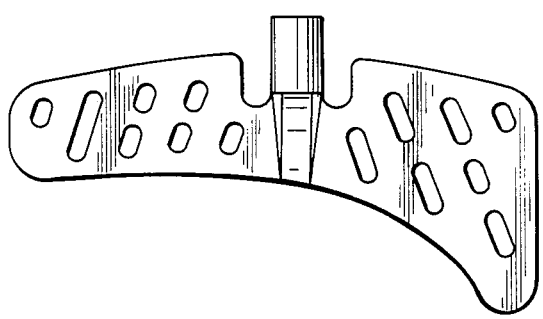
FIG. 18
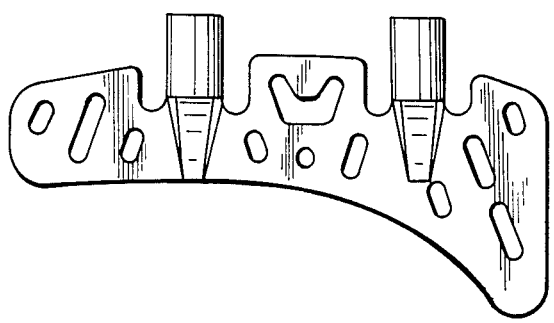

4,799,886

DENTAL SUBMERGED ENDOSSEOUS IMPLANT

BACKGROUND OF THE INVENTION

The present invention relates to dental implants.

At the present time various types of implants are used in dentistry and oral surgery. For example, a hole may be drilled in the patient's bone and a self-threading screw inserted and retained in the hole. The implant screw has a neck portion and an integral head portion which protrudes above the line of the gum. After the gum has healed, the head may be used to support the bridgework of artificial teeth. The angle of the head may be adjusted by bending the neck portion. Another type of implant is a flat blade-like body member which is positioned in a pre-cut groove in the bone. The blade-like body member has an integral head which protrudes above the gum line.

There have, over the years, been a series of studies indicating that it is preferable that the entire dental implant be "submerged", i.e., retained within the bone and below the gum, until after the gum has healed and at least some bone material has grown about the implant. The submerged implant is necessarily constructed in a number of pieces. For example, the procedure is as follows: a hole is drilled in the bone; a self-threading screw is screwed into the hole and a threaded hole at the top of the screw is closed with a removable plug. The gum is stitched closed ("sutured") and allowed to heal for 6 weeks to 6 months. Subsequently, the patient's gum is re-opened, the plug is removed and an abutment head member is mounted on the implanted screw. The head has a threaded shaft portion which screws into the bore of the screw implant, a neck portion and a head portion. The angle of the head portion may be adjusted by bending the neck portion.

SUMMARY OF THE INVENTION

The present invention provides a dental implant which is a submerged endosseous implant system. In operation, in one embodiment, a groove is formed in the jaw bone of the patient. The implant system, in one embodiment, uses an integral one-piece body member having a blade-like portion, a collar support portion, and one or more cylindrical tubular collars. Each cylindrical collar has an internal screw-threaded bore. After the blade body member is positioned in the groove, a short flat healing plug is screwed into the collar bore and the gum sutured and allowed to heal. After healing is complete, for example, 6 weeks to 6 months, the gum is opened, the flat-headed plug is removed and an abutment head assembly screwed into the collar bore. The head assembly includes an externally threaded shaft portion and a head portion having a groove. The head portion may be bent to obtain the desired head angle, the bend occurring at the groove of the head and not at a neck portion. The same type of abutment head may be used with a submerged screw implant.

OBJECTIVES AND FEATURES OF THE INVENTION

It is an objective of the present invention to provide an endosseous implant system which has a submerged implant body member to promote healing and long-term retention of the implant.

It is a further objective of the present invention to provide such an implant system having a blade member which blade will be sufficiently strong to prevent distortion of the blade after the restoration is complete and the patient uses his artificial teeth.

It is a further objective of the present invention to provide such a blade implant system which promotes healing, at the gum line and below the gum line, after the blade portion has been positioned in the bone.

It is a feature of the present invention to provide a one-piece integral submerged endosseous implant. In one embodiment a blade implant has, as portions thereof, a thin substantially flat elongated blade portion having top and bottom edges; a cylindrical collar portion at least part of which extends above the top edge and has a smooth external wall, a screw-threaded bore and top and bottom ends; and a collar support portion extending from the bottom end of the collar portion to the blade portion.

A flat-headed screw healing plug is screwed into the collar after the implant is positioned in a groove in the patient's bone. After healing, the plug is removed and a metal abutment head assembly having a head portion and a screw-threaded shaft portion is screwed into the collar bore.

The abutment head has a groove so that the top portion of the head may be bent at an angle at the groove. Preferably the groove is circumferential about the abutment head. All of the implant system members are of biocompatible titanium.

BRIEF DESCRIPTION OF THE DRAWINGS

Other objectives and features of the present invention may be derived from the following detailed description of the invention, taken in conjunction with the accompanying drawings.

In the drawings:

FIG. 1 is a front plan view of the body portion of the first embodiment of the present invention;

FIG. 2 is a side plan view of the implant body portion of FIG. 1;

FIG. 3 is a top plan view of the implant body portion of FIG. 1;

FIG. 4 is a front plan view of the implant body portion of FIG. 1 showing the distribution of the load at the bottom edge;

FIG. 7 is a front plan view of the abutment head;

FIG. 7A is a side plan view of the abutment head of FIG. 7;

FIG. 7B is a top plan view of the head of FIG. 7;

FIGS. 8–18 are front plan views, in a slightly reduced size compared to FIG. 1, of alternative implant body portions;

FIG. 19 is a front plan view, partly in cross-section, of an implant screw;

FIG. 19A is a bottom plan view of the implant screw of FIG. 19; and

FIGS. 20, 20A, and 20b are front, side and top plan views, respectively, of an abutment head which is used with the implant screw of FIG. 19, with FIG. 20 being partly in cross-section.

DETAILED DESCRIPTION OF THE INVENTION

Figure 5:
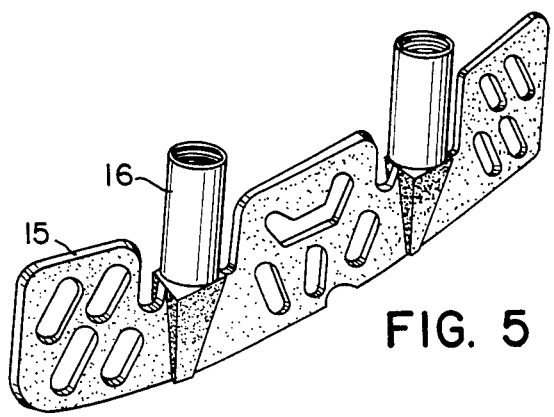
FIG. 5 is a perspective view of an alternative embodiment of the body portion.
Figure 6:
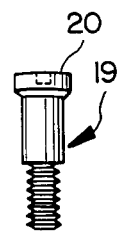
FIG. 6 is a perspective view of the healing closure plug.

As shown in FIGS. 1–7, the dental endosseous implant system of the present invention includes a body member 10 having a flat blade portion 11. The blade portion 11 is symmetric about the imaginary center line 12. The blade portion 11 has a series of internal round holes 13a–13d and two elongated holes 14a, 14b. The corners 15a–15d of the blades are rounded (seen in plan view in FIG. 1) and the edge 15 of the blade portion is flat. A tubular collar portion 16 is integral with the blade portion 11. The collar 16 is round in cross-section (See FIG. 2), has a smooth external surface, and merges with the rectangular collar support portion 17. The collar 16 has a bore 18 having internal screw threads.

The entire body portion 10 is designed to be submerged, i.e., positioned in a groove in the bone and enclosed below the gum. For example, an incision is made along the crest of the alveolar ridge and the gum flaps are reflected buccolingually. The groove is cut in the bone using a 700XL highspeed carbide bur, for initial preparation, and is finished to the appropriate depth with a 700XXL bur. The length (mesio-distal length) of the osseous groove should be about 1mm longer than the blade length. The implant is firmly seated with its shoulder (top edge of blade) about 1–2 mm countersunk below the alveolar crest. The gum is then sutured. After healing is complete, the mucossa covering is excized, the healing plug removed, the neck irrigated and the abutment head screwed into the collar. The abutment head is now ready for the final restoration work.

As mentioned above, after the implant body portion 10 is positioned in the groove, the collar bore 18 is filled with a removable closure-healing plug 19. The plug is screw 19 having a flat head 20, see FIG. 4. The gum is then sutured.

After healing is complete, the gum is opened and the screw 19 removed. The abutment head assembly 30 is then screwed into the bore 18.

As shown in FIGS. 5, 7, 7A and 7B, the abutment head 30 includes a head portion 31 and a shank portion 35. The head portion 31 has a groove 32 completely around its circumference which divides it into a top head portion 33 and a bottom head portion 34. The top head portion 33 may be bent, to any desired angle within the range 0 to 15 degress, from the axis and in any direction, at the groove 32. The groove, for example, is 0.090 inches in height and 0.040 inches in depth forming a central cylindrical portion 36 which is solid and round in cross-section and has a diameter of 0.080 inches. The top head portion 33 has a height of 0.185 inches. The bottom head portion 34 has a screw threaded shank portion 37. After such bending, the bridgework or other dental apparatus may be positioned on the entire head portion.

The entire implant system, including the body portion and head assembly, is preferably made of commercially pure biocompatible titanium. The top head portion may be bent at any desired angle within the range of 0°–15° for various alignment situations. The small cylindrical collar 16, with its smooth external surface, promotes complete and uniform subgum (subgingival) healing.

Figure 8:
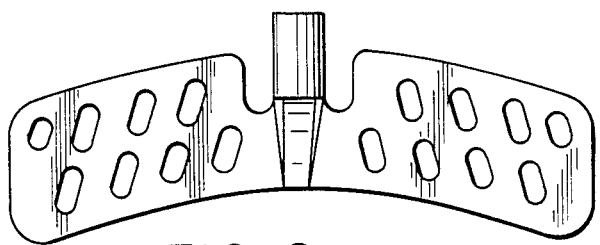
Figure 10:
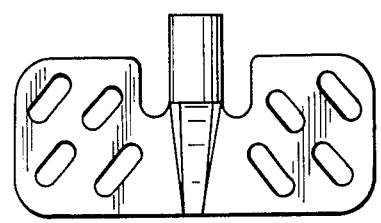
Figure 9:
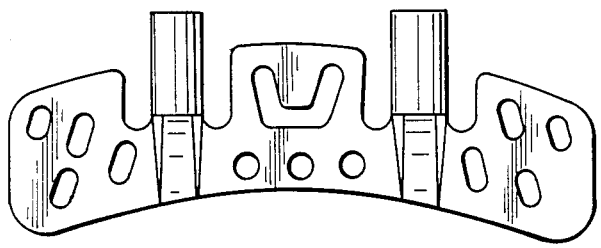
Figure 11:
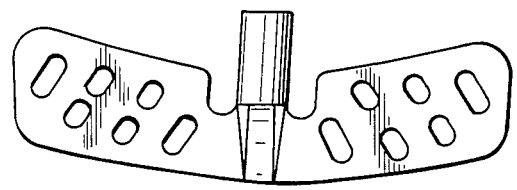

The implant system of the present invention may be used in various mandibular and maxiliary anatomical locations. Various embodiments, having one or two collars, and various shapes of blade portions, are shown in FIGS. 8–18.

The second embodiment of the present invention, using a submerged endosseous implant in the form of a screw 40, is shown in FIGS. 19, 19A, 20, 20A and 20B. As shown in FIG. 19, the screw body member 41 has an external helical thread 42. At its bottom the screw body member 41 has three evenly spaced outwardly projecting ribs 42a–42c which are also threaded. At its top the screw 40 has a threaded bore 43 to receive the healing plug 19 and subsequently, after healing, it receives the abutment head. A slit 44 is used to turn the screw.

The abutment head 50 for the screw 40 is shown in FIGS. 20, 20A and 20B.

The abutment head 50 includes a head portion 51 and a screw threaded shank portion 52. The head portion 51 has a groove 53 completely around its circumference which divides it into a top head portion 54 and a bottom head portion 55. The top head portion 54 may be bent, to any desired angle within the range 0 to 15 degrees from the axis and in any direction, at the groove 53. The groove, for example, is 0.090 inches in height and 0.030 inches in depth forming a central cylindrical portion 56 which is solid and round in cross-section and has a diameter of 0.089 inches. The top head portion 54 has a height of 0.185 inches. After such bending, the bridgework or other dental apparatus may be positioned on the entire head portion.

The entire screw implant system, including the body portion, plug and head, is preferably made of commercially pure biocompatible titanium. The top head portion 54 may be bent at any desired angle within the range of 0°–15° for various alignment situations.

An important feature of the abutment heads is that they have a flat face so that the head may be correctly orientated. The abutment head of FIGS. 7, 7A and 7B has a flat face 36 on its top head portion 33 and a flat face 36' on its bottom head portion 35. Abutment head 50 has flat face 57 on its top head portion 54.

Another important feature of the invention is that the blades are designed by finite element analysis.

What is claimed is:

1. A dental implant system comprising:
   a one-piece integral submerged endosseous blade implant having as portions thereof, a thin substantially flat elongated blade portion having top and bottom edges; a cylindrical collar portion at least part of which extends above said top edge and having a smooth external wall, a screw-threaded bore and top and bottom ends; and a collar support portion extending from the bottom end of the collar portion to the blade portion;
   a flat-headed screw healing plug which is screwed into said bore after the implant is positioned in a groove in the patient's bone;
   and a metal abutment head assembly having a head portion and a screw-threaded shaft portion, the shaft portion being screwed into said bore after the patient's gum is opened and the healing plug removed;
   wherein said head portion has a groove forming a top and a bottom head portion and the top head portion is bent at an angle to the bottom head portion at said groove, and wherein said groove is circumferential about the head and the top portion is bent at said groove in the range of 1 to 15 degrees.

2. A dental implant system as in claim 1, wherein all of said members are of biocompatible titanium.

3. A dental implant system as in claim 1, wherein said blade portion is symmetric about an imaginary center line.

4. A dental implant system as in claim 1, wherein said blade portion has a plurality of holes therethrough.

* * * * *